(12) United States Patent
Burgi

(10) Patent No.: US 8,398,650 B1
(45) Date of Patent: Mar. 19, 2013

(54) OFFSET CUP IMPACTOR WITH AN EXPANDABLE DOME FOR DOUBLE MOBILITY IMPLANTS

(75) Inventor: Jonas Burgi, Moutier (CH)

(73) Assignee: Greatbatch Medical S.A., Orvin (CH)

( * ) Notice: Subject to any disclaimer, the term of this patent is extended or adjusted under 35 U.S.C. 154(b) by 368 days.

(21) Appl. No.: 12/694,524

(22) Filed: Jan. 27, 2010

Related U.S. Application Data

(60) Provisional application No. 61/147,504, filed on Jan. 27, 2009.

(51) Int. Cl.
*A61B 17/58* (2006.01)
(52) U.S. Cl. .......................................... 606/99; 606/91
(58) Field of Classification Search .................. 606/81, 606/89, 91, 99, 100; 623/22.12, 22.21–22.39
See application file for complete search history.

(56) References Cited

U.S. PATENT DOCUMENTS

| 1,942,422 | A | 6/1931 | Hanna |
| 4,305,394 | A | 12/1981 | Bertuch, Jr. |
| D272,648 | S | 2/1984 | Bolesky et al. |
| D273,806 | S | 5/1984 | Bolesky et al. |
| 4,475,549 | A | 10/1984 | Oh |
| 4,520,511 | A | 6/1985 | Gianezio et al. |
| 4,528,980 | A | 7/1985 | Kenna |
| 4,587,964 | A | 5/1986 | Walker et al. |
| 4,632,111 | A | 12/1986 | Roche |
| 4,716,894 | A | 1/1988 | Lazzeri et al. |
| 4,765,328 | A | 8/1988 | Keller et al. |
| 4,904,267 | A | 2/1990 | Bruce et al. |
| 4,919,679 | A | 4/1990 | Averill et al. |
| 4,921,493 | A | 5/1990 | Webb, Jr. et al. |
| 5,019,105 | A | 5/1991 | Wiley |
| 5,037,424 | A | 8/1991 | Aboczsky |
| 5,061,270 | A | 10/1991 | Aboczky |
| 5,062,854 | A | 11/1991 | Noble et al. |
| 5,089,003 | A | 2/1992 | Fallin et al. |
| 5,116,339 | A | 5/1992 | Glock |
| 5,124,106 | A | 6/1992 | Morr et al. |
| 5,133,766 | A | 7/1992 | Halpern |
| 5,169,399 | A | 12/1992 | Ryland et al. |
| 5,190,549 | A | 3/1993 | Miller et al. |
| 5,234,432 | A | 8/1993 | Brown |
| 5,261,915 | A | 11/1993 | Durlacher et al. |
| 5,324,293 | A | 6/1994 | Rehmann |
| 5,342,362 | A | 8/1994 | Kenyon et al. |
| 5,364,403 | A | 11/1994 | Petersen et al. |
| 5,417,696 | A | 5/1995 | Kashuba et al. |
| 5,443,471 | A | 8/1995 | Swajger |
| 5,454,815 | A | 10/1995 | Geisser et al. |

(Continued)

FOREIGN PATENT DOCUMENTS

| EP | 0453694 | 10/1991 |
| EP | 0470912 | 12/1992 |

(Continued)

OTHER PUBLICATIONS

European Search Report dated Apr. 15, 2011.

*Primary Examiner* — Kevin T Truong
*Assistant Examiner* — Diana S Jones
(74) *Attorney, Agent, or Firm* — Michael F. Scalise

(57) ABSTRACT

An orthopaedic prosthetic inserter used for the implantation of double mobility implants is described. The inserter consists of a drive train, a C-shaped housing, and a prosthetic cup grabbing subassembly. The subassembly comprises a frustro-conical nose and an expandable dome. When activated by the drive train, the dome expands into the cup of the prosthetic to manipulate the prosthetic during implantation.

22 Claims, 9 Drawing Sheets

U.S. PATENT DOCUMENTS

| | | |
|---|---|---|
| 5,485,887 A | 1/1996 | Mandanis |
| 5,540,697 A | 7/1996 | Rehmann et al. |
| 5,584,837 A | 12/1996 | Petersen |
| 5,658,294 A | 8/1997 | Sederholm |
| 5,665,091 A | 9/1997 | Nobel et al. |
| 5,683,399 A | 11/1997 | Jones |
| 5,707,374 A | 1/1998 | Schmidt |
| 5,720,750 A | 2/1998 | Koller et al. |
| 5,863,295 A | 1/1999 | Averill et al. |
| 5,913,860 A | 6/1999 | Scholl |
| 5,976,148 A | 11/1999 | Charpenet et al. |
| 5,993,455 A | 11/1999 | Noble |
| 6,063,124 A | 5/2000 | Amstutz |
| 6,120,508 A | 9/2000 | Grunig et al. |
| 6,197,065 B1 | 3/2001 | Martin et al. |
| 6,432,141 B1 | 8/2002 | Stocks et al. |
| 6,451,058 B2 | 9/2002 | Tuke et al. |
| 6,626,913 B1 | 9/2003 | McKinnon et al. |
| 6,663,636 B1 | 12/2003 | Lin |
| 6,811,569 B1 | 11/2004 | Afriat et al. |
| 7,192,449 B1 | 3/2007 | McQueen et al. |
| 7,335,207 B1 | 2/2008 | Smith |
| 7,341,593 B2 | 3/2008 | Auxepaules et al. |
| 7,396,357 B2 | 7/2008 | Tornier et al. |
| 7,585,301 B2 | 9/2009 | Santarella et al. |
| 7,591,821 B2 | 9/2009 | Kelman |
| 7,604,667 B2 | 10/2009 | DeSmet et al. |
| 7,621,921 B2 | 11/2009 | Parker |
| 7,922,726 B2 | 4/2011 | White |
| 2001/0051830 A1 | 12/2001 | Tuke et al. |
| 2002/0004660 A1 | 1/2002 | Henniges et al. |
| 2002/0177854 A1 | 11/2002 | Tuke et al. |
| 2002/0193797 A1 | 12/2002 | Johnson |
| 2003/0009234 A1 | 1/2003 | Treacy et al. |
| 2003/0050645 A1 | 3/2003 | Parker et al. |
| 2003/0083668 A1 | 5/2003 | Rogers et al. |
| 2003/0088316 A1 | 5/2003 | Ganjianpour |
| 2003/0187512 A1 | 10/2003 | Frederick et al. |
| 2003/0220698 A1 | 11/2003 | Mears et al. |
| 2003/0229356 A1 | 12/2003 | Dye |
| 2004/0215200 A1* | 10/2004 | Tornier et al. .................. 606/91 |
| 2005/0038443 A1 | 2/2005 | Hedley et al. |
| 2005/0075736 A1 | 4/2005 | Collazo |
| 2005/0137603 A1 | 6/2005 | Belew et al. |
| 2005/0171548 A1 | 8/2005 | Kelman |
| 2005/0187562 A1 | 8/2005 | Grimm et al. |
| 2005/0222572 A1 | 10/2005 | Chana |
| 2005/0228395 A1 | 10/2005 | Auxepaules et al. |
| 2005/0234462 A1 | 10/2005 | Hershberger |
| 2005/0246031 A1 | 11/2005 | Frederick et al. |
| 2006/0052780 A1 | 3/2006 | Errico et al. |
| 2006/0149285 A1* | 7/2006 | Burgi et al. ..................... 606/99 |
| 2007/0156155 A1 | 7/2007 | Parker |
| 2007/0167952 A1 | 7/2007 | Burgi et al. |
| 2007/0225725 A1 | 9/2007 | Heavener et al. |
| 2007/0270783 A1 | 11/2007 | Zumsteg et al. |
| 2007/0288096 A1 | 12/2007 | Surma |
| 2007/0293869 A1 | 12/2007 | Conte et al. |
| 2008/0004628 A1 | 1/2008 | White |
| 2008/0021481 A1 | 1/2008 | Burgi |
| 2008/0033444 A1 | 2/2008 | Bastian et al. |
| 2008/0077249 A1 | 3/2008 | Gradel |
| 2008/0146969 A1 | 6/2008 | Kurtz |
| 2008/0154261 A1 | 6/2008 | Burgi |
| 2008/0243127 A1 | 10/2008 | Lang et al. |
| 2008/0255565 A1 | 10/2008 | Fletcher |
| 2008/0255568 A1 | 10/2008 | Tornier et al. |
| 2008/0262503 A1 | 10/2008 | Muller |
| 2008/0275450 A1 | 11/2008 | Myers et al. |
| 2009/0112214 A1 | 4/2009 | Philippon et al. |
| 2009/0182334 A1 | 7/2009 | Brehm |
| 2009/0192515 A1 | 7/2009 | Lechot et al. |
| 2009/0240256 A1 | 9/2009 | Smith |
| 2009/0281545 A1 | 11/2009 | Stubbs |
| 2009/0281550 A1* | 11/2009 | Keller ............................. 606/99 |

FOREIGN PATENT DOCUMENTS

| | | |
|---|---|---|
| EP | 0535973 | 4/1993 |
| EP | 357302 A1 | 7/1994 |
| EP | 638299 A1 | 2/1995 |
| EP | 1308140 A1 | 5/2003 |
| EP | 1190687 B1 | 7/2004 |
| EP | 1438936 | 7/2004 |
| EP | 1447058 A1 | 8/2004 |
| WO | 9511641 | 5/1995 |
| WO | WO0012832 A2 | 3/2000 |
| WO | 0106964 | 2/2001 |
| WO | WO2005044153 | 5/2005 |
| WO | 2006061708 | 6/2006 |
| WO | WO2007098549 A1 | 9/2007 |
| WO | WO2008128282 A1 | 10/2008 |
| WO | 2009136284 | 11/2009 |

* cited by examiner

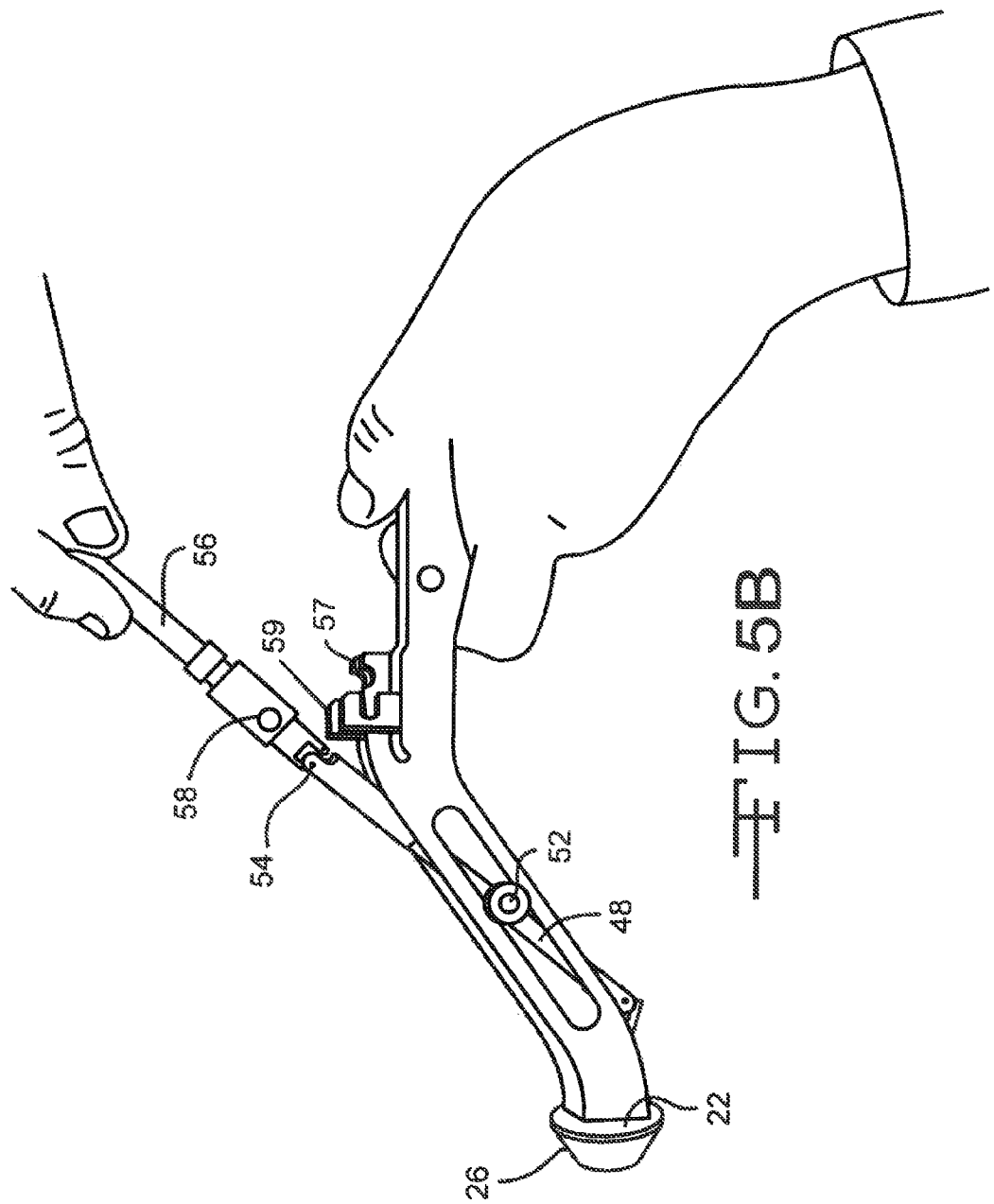

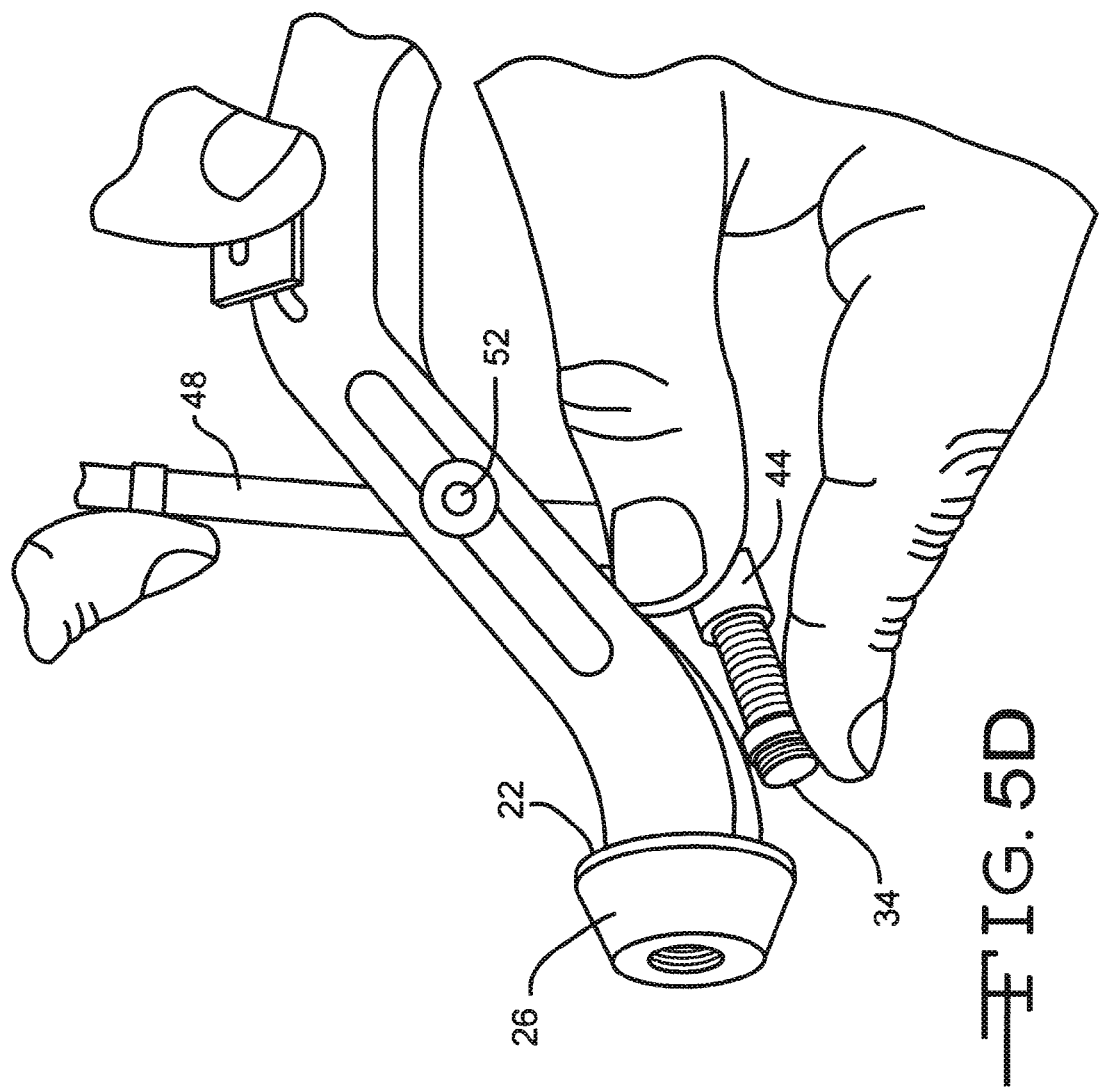

US 8,398,650 B1

OFFSET CUP IMPACTOR WITH AN EXPANDABLE DOME FOR DOUBLE MOBILITY IMPLANTS

CROSS REFERENCE TO RELATED APPLICATIONS

This application claims priority to U.S. provisional application Ser. No. 61/147,504, filed on Jan. 27, 2009.

BACKGROUND OF THE INVENTION

This invention relates to surgical inserters for aiding in installing orthopedic prostheses, and more specifically, to easily sterilizable inserters for installing acetabular implants in the acetabular socket.

A double mobility prosthetic cup is a type of acetabular implant that is designed to increase a patient's range of mobility. Unlike other types of actabular implants, double mobility prosthetic cups do not have an opening through the cup portion which allows for easy manipulation during implantation. For example, a rod is typically threaded through the cup opening. This rod is used like a handle with which to control and guide the implant during implantation. Double mobility implants, on the other hand, do not have such an opening and therefore create a challenge in controlling them during implantation. The present invention solves this problem and provides an effective novel means of manipulating the double mobility implant during implantation.

Complicated mechanical devices have crevices and recesses that are difficult, if not almost impossible to clean with ease. Devices that are not properly cleaned and sterilized run the risk of disease transfer from patient to patient following the emergence of certain "prions" that are not killed by normal hospital sterilization and need to be physically removed by washing and rinsing.

Further, in surgical procedures in which access to the treatment site is limited, it is difficult to use current solutions without subjecting the patient to repeated abrasion and tissue trauma when inserting and extracting surgical instruments.

Still further, once the appropriate position of the implant is selected, it is often difficult to ensure that the position does not change upon insertion of the assembly through the incision.

What is needed therefore is a double mobility implant inserter that is easily adjustable, disassemblable, and cleanable. Further, what is needed is an inserter that enables the surgeon to better maneuver, position and install the double mobility implant in a particular angular orientation.

SUMMARY OF THE INVENTION

The present invention relates to an acetabular inserter that aids a surgeon in controlling the installation of a double mobility acetabular cup prosthesis. The inserter has a housing which encloses a drive train having, at a far end, a double mobility prosthetic engaging subassembly, and at the opposite end, a handle which facilitates activation of the drive train and movement of the subassembly. The inserter enables easy orientation of a double mobility prosthesis attached to its end. This is important because precise control of the prosthetic is critical in implantation of the prosthetic in a patient.

The subassembly comprises a series of components, a frustro-conical nose and an expandable dome which work in concert to grip the inside of the prosthetic cup.

An objective of the invention is to be "easily cleaned" by quick and modular disassembly which enables access to all surfaces that can be cleaned. The reduction in the number of small radius internal corners, crevices and small gaps and the absence of blind holes also aids in the sterilization of the instrument.

BRIEF DESCRIPTION OF THE DRAWINGS

The attached drawings represent, by way of example, different embodiments of the subject of the invention.

FIG. 5B is a perspective view of the inserter of the present invention, showing another step of disassembly for cleaning.

FIG. 5D is a perspective view of the inserter of the present invention, showing a stage of disassembly for cleaning.

DETAILED DESCRIPTION OF THE PREFERRED EMBODIMENT(S)

Figure 1A:
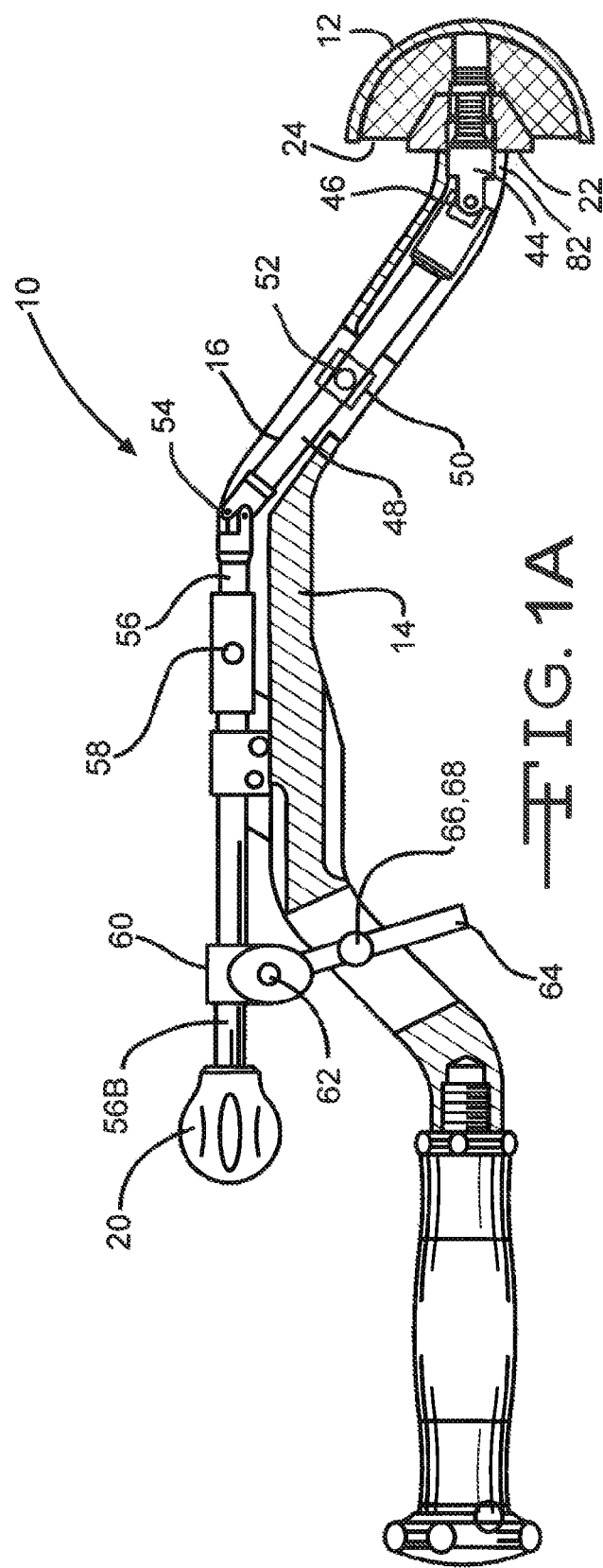
FIG. 1A is a cross-sectional side view of the inserter of the invention.
Figure 1B:
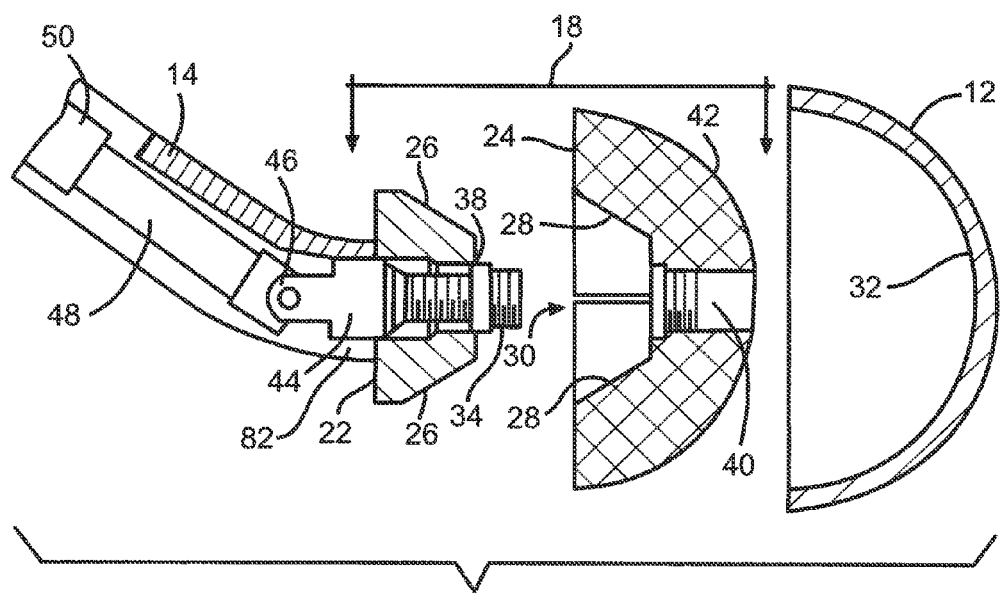
FIG. 1B is a magnified cross-sectional side view of the components that comprise the subassembly.
Figure 1C:
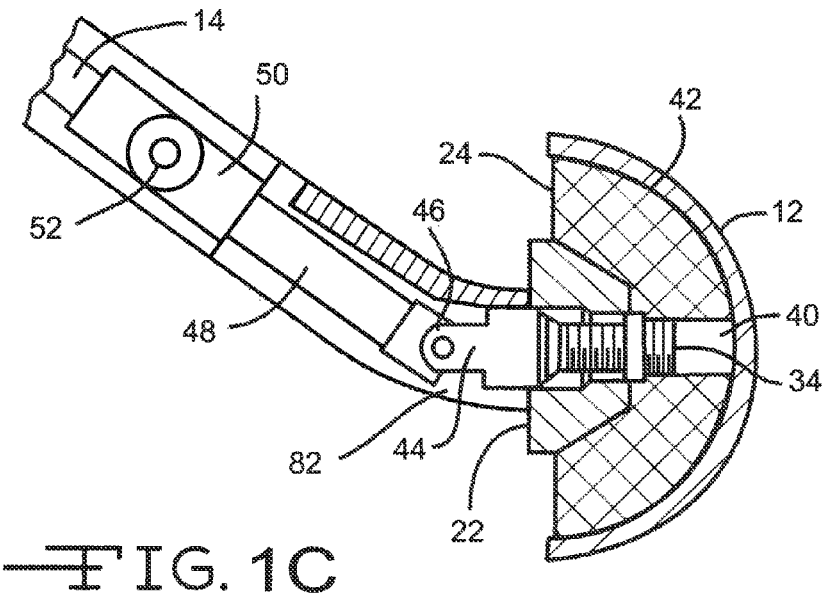
FIG. 1C is a magnified cross-sectional side view of the components of the subassembly aligned together.

Referring now to FIGS. 1A-1C, an acetabular inserter 10 is provided to aid the surgeon in controlling the installation of an acetabular cup prosthesis 12. The inserter 10 has a housing 14 which encloses a drive train 16 having, at a distal end, a prosthesis engaging subassembly 18, and at the proximal end, a handle 20 which facilitates moving of the drive train by the operator. The housing 14 may be C-shaped, as shown, in order to minimize the invasiveness of the surgery by better clearing anatomical structures and tissue.

The subassembly 18 comprises a nose 22 and a dome 24 that are in direct communication with each other. The dome 24 is designed to expand into the double mobility acetabular cup prosthesis 12 to provide a substantially friction tight engagement which enables precise control of the prosthesis 12 during implantation in the body.

The distal end of the nose 22 has a frustro-conical shape that engages the dome 24 in its proximal end. The nose 22 has an annular ramp surface 26 that slopes downwardly and inwardly towards the distal end of the nose 22. The downwardly sloping ramp surface 26 engages the proximal end of the dome 24 by contacting the opposing coping surface 28 inside the dome cavity 30 located at the proximal end of the dome 24. The dome cavity 30 is designed to receive the frustro-conical shape of the distal end of the nose 22. As will be discussed in more detail, the downwardly and inwardly shape of the ramp surface 26 acts as a wedge to expand the dome 24. The outwardly expansion of the dome 24 creates a friction tight engagement between the dome 24 and the interior cup surface 32.

The nose 22 is connected to the distal end of the housing 14. A cylindrical rod 34, which is connected to a cylindrical piston 44, slides in an axial bore 38 that penetrates through the nose 22 and into the dome 24. The cylindrical rod 34 is preferably threaded. In a preferred embodiment, the nose 22 is made of a polymer material. However, alternate materials such as metal or ceramic could also be used to create the nose 22.

A channel 40 penetrates through the center of the dome 24 from the distal end of the dome cavity 30 through the outer distal dome surface 42. The channel 40 provides a space for the cylindrical rod 34 to reside and gives added flexibility to the expansion of the dome 24 as well. It is preferred that channel 40 have grooves to receive the threads of the cylindrical rod 34.

Figure 5A:
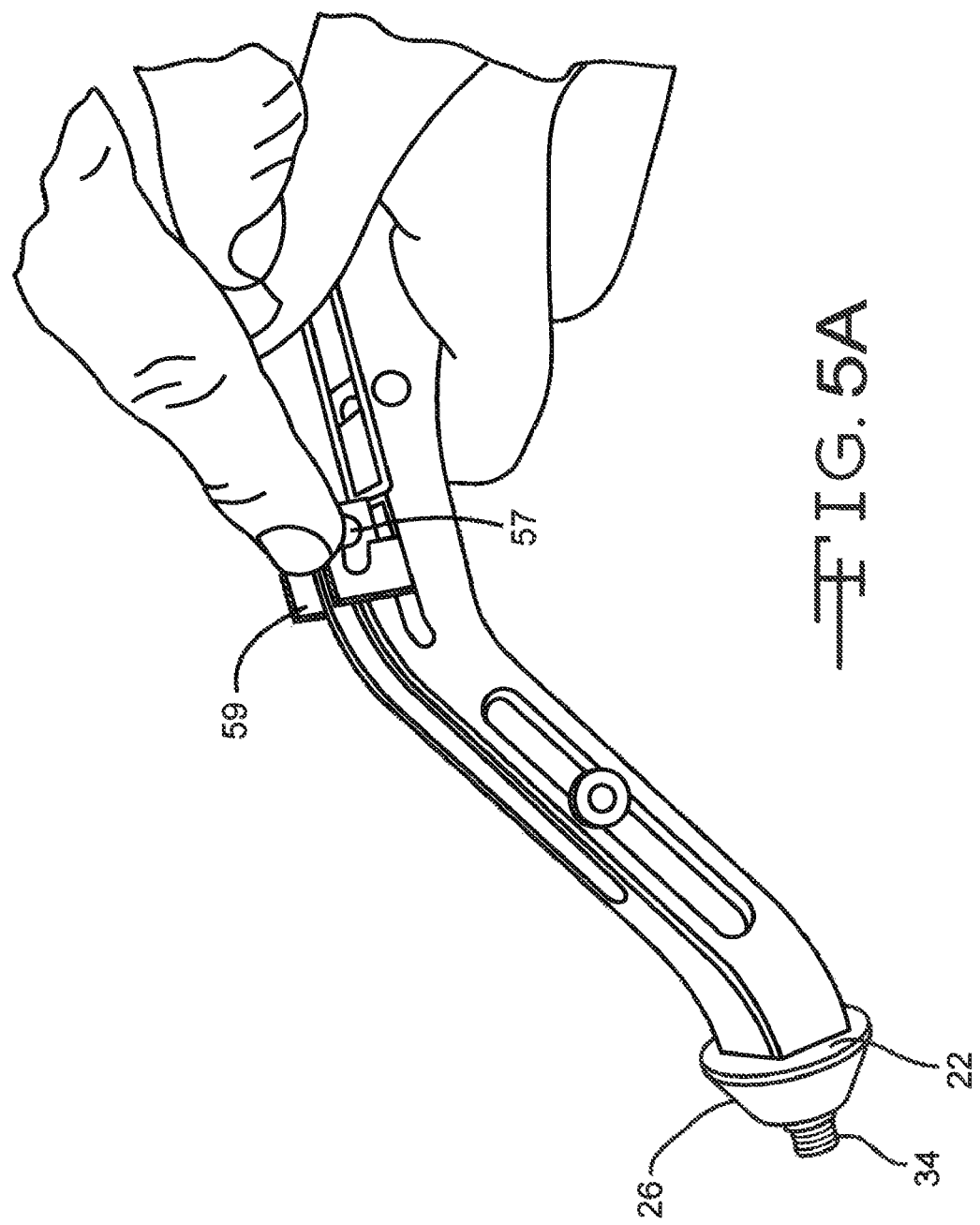
FIG. 5A is a perspective view of the inserter of the present invention, showing a step of disassembly for cleaning.
Figure 5C:
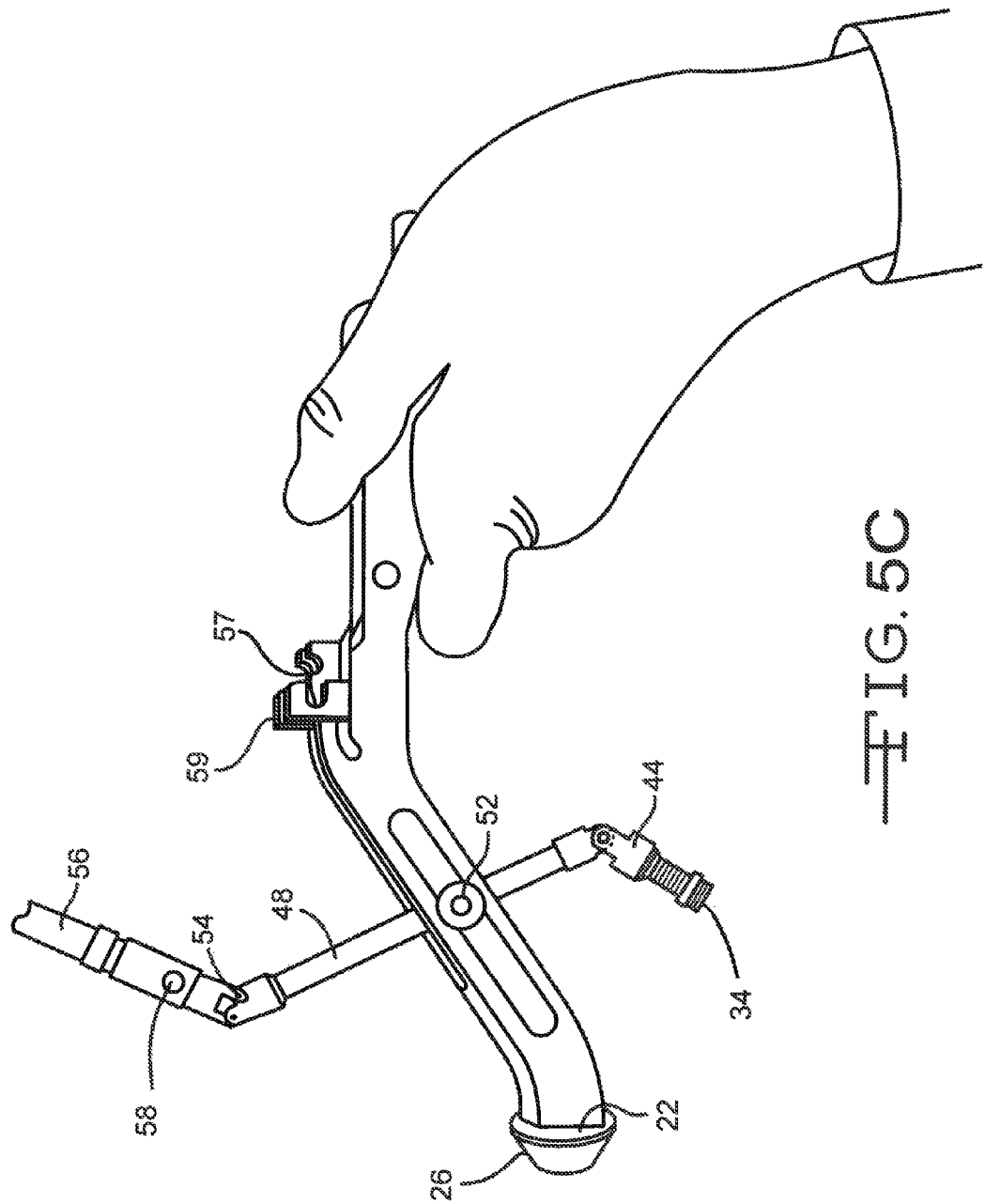
FIG. 5C is a perspective view of the inserter of the present invention, showing a stage of disassembly for cleaning.

The piston 44 is connected by way of a first O-joint 46 to a lever 48 which slides in a pivoting sleeve 50 fixed to the housing 14 via a pivot 52. The lever 48 is connected via a second U-joint 54 to a second pivoting lever 56 which is fixed to pivot, in a catch 57 (FIG. 5A) on a pivot pin 58. The catch is essentially a divot or a seat cut into the housing 14, against which the pivot pin 58 of the lever 56 is captured when a slide 59 (FIG. 5A) is slid over the pin 58 when engaged against the seat.

A slideable sleeve 60 (FIGS. 1A and 4) slides over the lever 56 and has a trunnion 62 to which a rod 64 is pivotally attached. The rod 64 passes through a one-way catch 66 in the housing 14. The one-way catch 66 can be a captured split wedge sleeve 68 having an inner diameter that just matches the outer diameter of the rod 64 and which is captured in a recess having a matching conical surface that surrounds the sleeve so as to allow the rod 64 to slide into the housing 14, but to prevent the rod 64 from sliding out of the housing 14 unless an unlock lever (not shown) is activated, such lever merely lifting the sleeve 68 out of engagement with the conical surface so as not to lock and to permit the rod 64 to back out of the housing 14. Any number of alternative one-way lock devices may be used however, the selection of which being within the skill of a person of ordinary skill in this field.

Figure 2A:
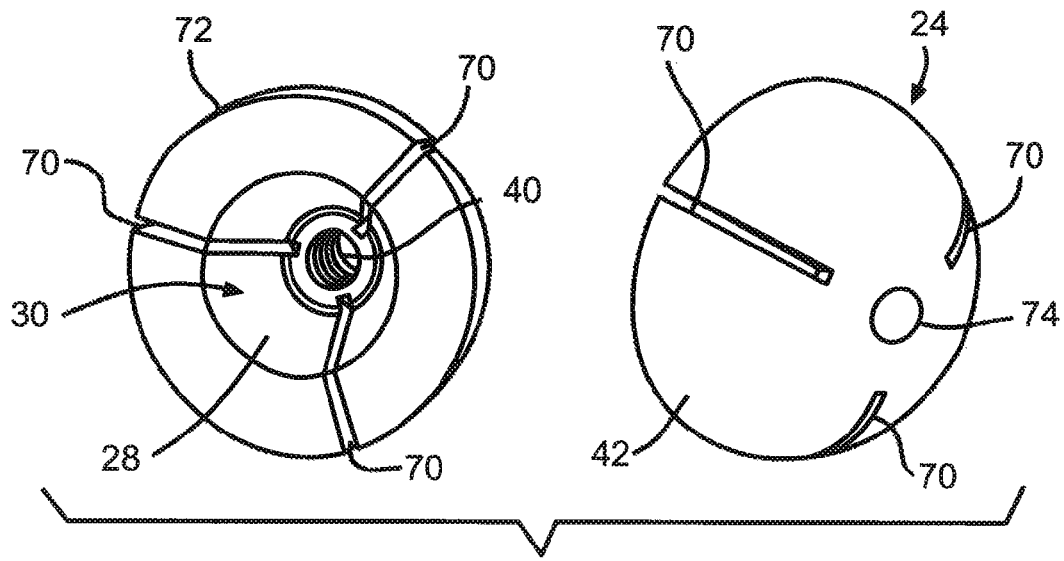
FIG. 2A is a perspective view of the proximal and distal ends on the expandable dome.
Figure 2B:
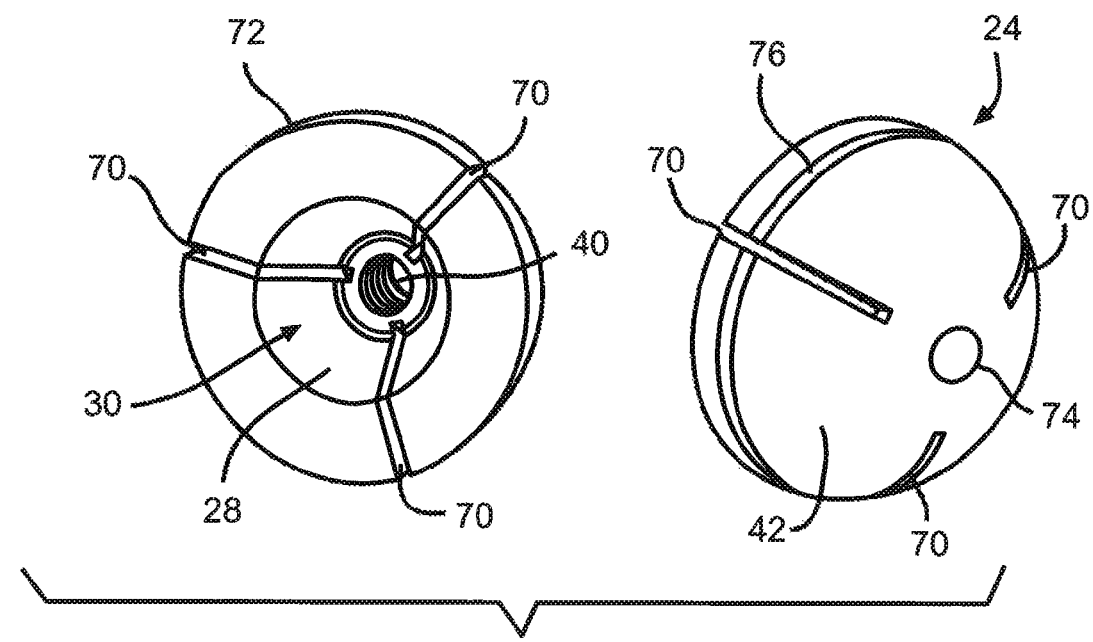
FIG. 2B shows a perspective view of the proximal and distal ends of an alternate embodiment of the expandable dome.

FIGS. 2A and 2B depict different preferred embodiments of the dome 24. The dome 24 is made out of a pliable polymer material which is designed to fit and expand into the prosthetic cup 12 to create a substantially friction tight engagement between the dome 24 and the interior cup surface 32 that is incapable of movement with respect to the subassembly 18. The dome 24 is designed to be sized to fit a multitude of different double mobility implants 12 of different diameters and depths. As such, the diameter of the dome 24 may range from about 2 cm to about 15 cm. The depth of the dome 24 may range from about 2 cm to about 10 cm. In all cases, it is preferred that the dome 24 create an interference fit with the interior of the prosthetic cup surface 32.

The dome 24 is designed with at least one slit 70 through the distal surface of the dome 24. The slit or slits 70 have a width from about 1 mm to about 10 mm that penetrates through the distal dome surface 42 through the dome body from the proximal dome end through the distal dome end to a core region that is just above the channel 40 of the dome 24. In other words, each slit 70 penetrates from the distal dome surface 42 to the core region of the dome. The slits 70 divide the dome 24 into sections 72 that are capable of independent or unison movement. It is preferred that the dome 24 have three slits 70. However, one could design the dome 24 with two, four, five, six or more slits 70 as desired. As previously mentioned, the dome channel 40 and opening 74 provide added flexibility to the dome sections 72.

The proximal end of the dome 24 has a rounded cavity 30 in which the distal end of the nose 22 resides. The threaded end of the cylindrical rod 34 resides in the bore 38 of the dome 24. The threads of the cylindrical rod 34 engage the grooves in the dome channel 40.

When activated, the cylindrical rod 34 slides proximally towards the distal end of the housing 14. The rod 34 traverses through the bore 38 of the nose 22, pulling the attached dome 24 proximally towards the ramp surface 26 of the nose 22. The coping surface 28 of the dome 24 inside the cavity 30 meets the ramp surface 26 of the nose 22 creating a force therebetween. This force separates and moves the sections 72 of the dome 24 distally thereby expanding the diameter of the dome 24 against the interior cup surface 32 creating a seal therebetween.

Although the nose 22 and dome 24 components are preferably frusto-conical and dome, in shape respectively, alternate forms and shapes of these components could also be used. What is required of the invention are matching components, one with a ramping surface, the other with a coping surface, that work together to expand outwardly to grasp the interior surface of the prosthetic 32. For example, instead of a dome shaped component, one could design a cone shaped component with a proximal coping surface working in conjunction with a triangular shaped component with a ramp surface that rides along the opposing coping surface, expanding the cone shaped component. The expandable component being of an appropriate size and form to create a frictional interference fit with the interior cup surface 32. Furthermore, the nose 22 and dome 24 could be of a variety of curved, rounded or conical shapes.

In an alternate embodiment as shown in FIG. 23, an O-ring 76 is received in an annular groove 78 on the surface of the distal end of the dome 24. The O-ring 76 is designed to improve the seal by creating a more uniform frictional fit with the interior cup surface 32. The O-ring 76 is made from a polymer material, preferably silicone rubber, that is capable of expanding in unison with the dome 24. As such, the O-ring 76 has a diameter which creates an interference fit with the interior cup surface 32. The thickness of the O-ring 76 is from about 1 mm to about 10 mm.

Figure 3A:
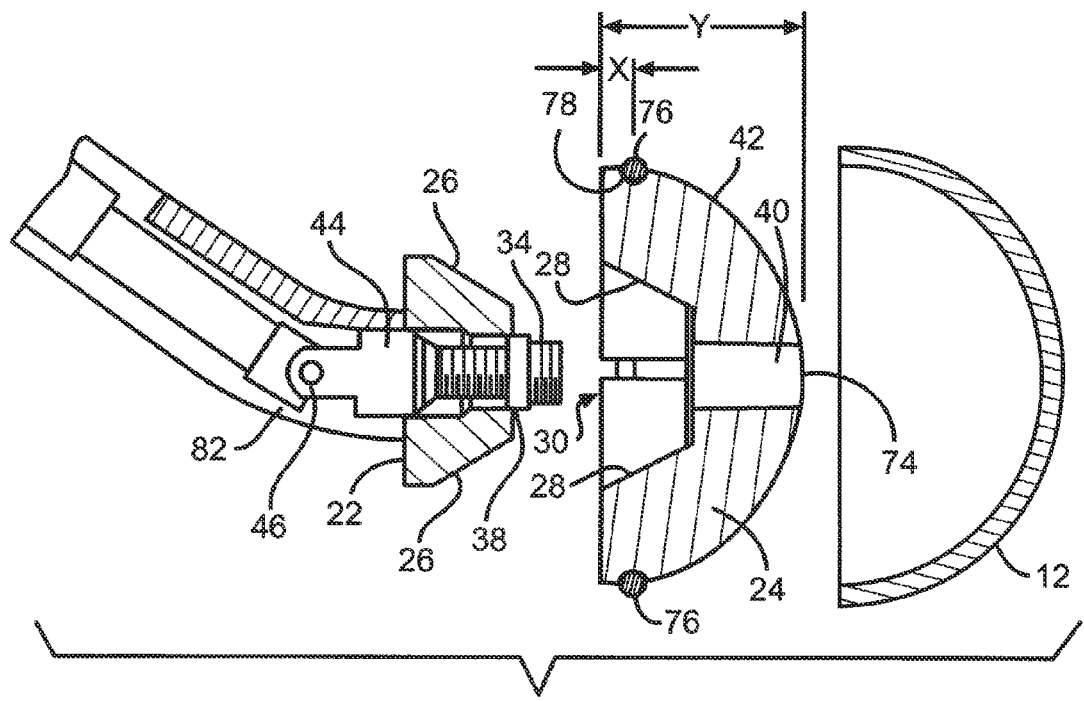
FIG. 3A is a magnified cross-sectional side view of the components that comprise an alternate embodiment of the subassembly.

The O-ring 76 is positioned on the outer distal surface 42 of the dome 24 near the proximal end. This creates an improved frictional seal that does not damage the prosthetic cup 12. As shown in FIG. 3A, it is preferred that the O-ring 76 be placed a distance x from the proximal end of the dome 24. The distance x is defined to be from about 1 to about 25 percent of y, the distance along a longitudinal axis from the proximal end to the apex of the dome 24.

Figure 3B:
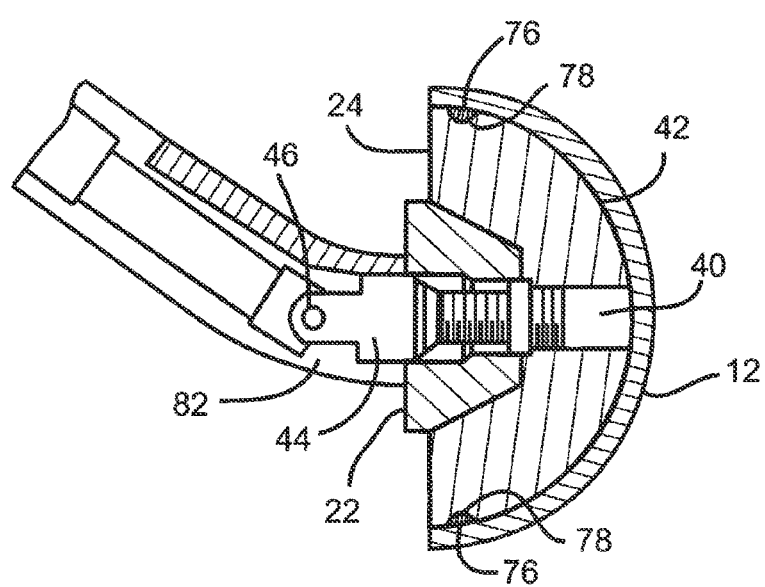
FIG. 3B is a magnified cross-sectional side view of the components that comprise an alternate embodiment of the subassembly aligned together.

The cross-sectional views of FIGS. 3A-3B illustrate how the alternate dome 24 embodiment is utilized in the subassembly 18. As shown in FIG. 3A, the O-ring 76 is positioned in the annular groove 78 surrounding the outside distal dome surface 42.

Although an O-ring 78 is preferred in the present invention, one skilled in the art might design a different attachment to the dome 24. For example, one might attach a wide band or flap around the dome 24 to form a seal between the dome 24 and interior cup surface 32.

Figure 4:
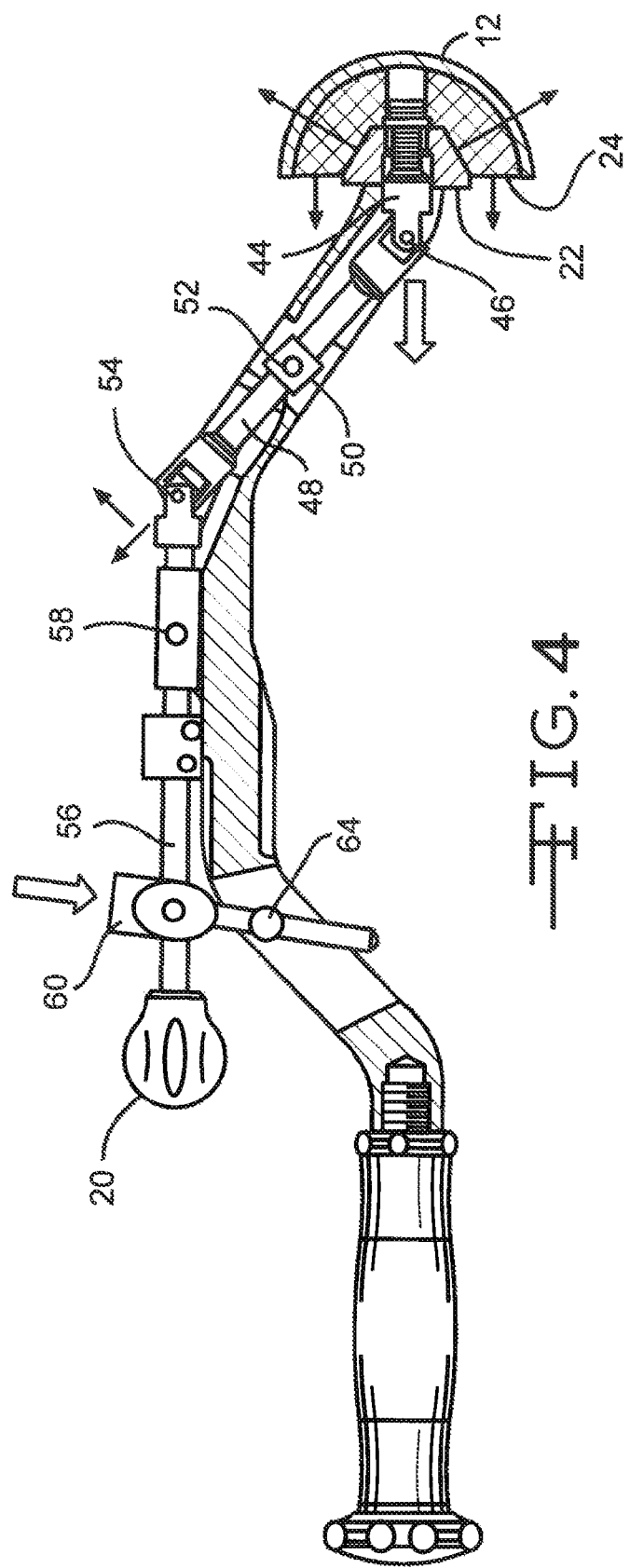
FIG. 4 is a cross-sectionai view of the inserter of the present invention in operation.

Referring now to FIG. 4, in operation, first the dome 24 is threaded onto the threaded cylindrical rod 34 in such a manner that the dome ramp surface 26 is in contact with the coping surface 28 of the dome 24. The operator may rotate the handle 20 about its axis to turn the drive train 14 in order to orient the prosthesis in what he believes to be a correct or an initial position. Then, the proximal end 56B of the lever 56 is urged downwardly toward the housing 14. Such downward movement acts through the drive train 16 to draw the piston 44 into the housing 14, and thus to cause the coping surface 28 of the dome 24 to be drawn against the ramp surface 26 of the nose 22 so as to create a normal force between the inside of the dome 24 and the nose 22. This normal force causes the sections 72 and outer distal surface of the dome 42 to expand outwardly so as to grip the interior cup surface 32 of the prosthetic cup 12. The operator may use the one way locking mechanism 68 to lock the lever 56 in a position so as to lock the dome 24 against the nose 22, thus enabling the surgeon to pre-set and lock the position of the prosthesis 12 prior to the installation thereof.

Referring now to FIGS. 5A-5D, in the embodiment shown, the device 10 is disassembled for cleaning by simply sliding the slide 59 back so as to release the pivot 52 and then lift the drive train 16 out of the housing but allow it to remain pivotally connected at pivot 52. As the drive train 16 is pivoted, the piston 44 is drawn out of the housing cavity 82. To reassemble after cleaning, the piston 44 is reinserted into the housing cavity 82 and the drive train 16 is rotated back into position, with the one way locking mechanism entering its receiver and the pivot 52 again entering into the catch 57. The slide 59 is then slid over the pivot 52 and the inserter 10 is again ready for use.

The present invention can be packaged in a kit offering a variety of double mobility prosthetic implants 12 of different sizes and diameters. The inserter 10, and assorted double mobility implants 12 and domes 24 can be packaged in a case with recesses which conveniently holds the components in a convenient easy to access manner.

The attached drawings represent, by way of example, different embodiments of the subject of the invention. Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An inserter for aiding a surgeon in controlling the installation of a prosthesis cup, the inserter comprising:
   a) a housing extending from a proximal housing end to a distal housing end;
   b) a nose supported at the distal housing end with a bore extending longitudinally through the nose, wherein the nose comprises an outer ramping surface extending distally and inwardly toward the bore from a proximal nose end adjacent to the housing to a distal nose end;
   c) an expandable dome having comprising a dome length extending distally and inwardly from a proximal end adjacent to the housing to an apex of the dome, wherein the inner dome surface comprises a coping surface extending from the proximal end part way along the dome length toward the apex, the dome being supported on the nose with the inner coping surface contacting the outer ramp surface of the nose;
   d) an O-ring supported in an annular groove provided in the outer dome surface;
   e) a drive train at least partially housed inside the housing, the drive train comprising:
      i) a first lever comprising a first lever proximal end spaced apart from a first lever distal end located adjacent to the distal housing end;
      ii) a second lever comprising a second lever proximal end located adjacent to the proximal housing end and spaced apart from a second lever distal end;
      iii) a drive rod comprising a drive rod proximal end space apart from a drive rod distal end, wherein the second lever distal end is in a universal joint relationship with the first lever proximal end, and wherein the first lever distal end is in a universal joint relationship with the drive rod proximal end and the drive rod distal end extends through the bore of the nose and connects to the dome in the dome bore;
      iv) a first sleeve pivotably connected to the housing, wherein the first lever is in a slidable relationship with a first opening in the first sleeve disposed at an intermediate location between the first lever proximal end and the first lever distal end;
      v) wherein the second lever is pivotably supported by the housing; and
   f) wherein the second lever proximal end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod to move along the longitudinal bore in the nose with the drive rod distal end connected to the dome moving from a first drive rod position spaced from the nose to a second drive rod position closer to the nose than the first drive rod position to thereby cause the inner coping surface of the dome to move proximally against the outer ramp surface of the nose to thereby cause the dome supporting the O-ring to both expand from a first, unexpanded state to a second expanded state.

2. The inserter of claim 1 wherein the ramping surface of the nose has a frusto-conical shape.

3. The inserter of claim 1 wherein the housing is C-shaped.

4. The inserter of claim 1 wherein the dome is made of a polymeric material.

5. The inserter of claim 1 wherein actuation of the drive train draws the drive rod along the bore in the nose to thereby move the dome in a proximal direction with the inner coping surface of the dome riding against the outer ramping surface of the nose to thereby expand the dome from a first state to a second state of a larger size than the first state against a prosthesis cup and into a substantially friction tight engagement therebetween.

6. The inserter of claim 1 wherein the dome has at least one slit that penetrates into the dome from the distal dome surface through to the core region of the dome.

7. The inserter of claim 1 wherein the O-ring is positioned around an outside circumference of the dome a distance x from the proximal end of the dome, the distance x being from about 1 to about 25 percent of y, which is the distance along the longitudinal axis from the proximal end to the apex of the dome.

8. The inserter of claim 1 wherein the O-ring is of a polymer material.

9. The inserter of claim 1 wherein a knob is attached to the second lever proximal end, the knob enabling a user to manipulate the drive train.

10. The inserter of claim 1 wherein the material of the nose is selected from the group consisting of a polymer, a metal and a ceramic.

11. An inserter for aiding a surgeon in controlling the installation of an orthopaedic prosthesis, the inserter comprising:
   a) a housing extending from a proximal housing end to a distal housing end;
   b) a frusto-conical nose supported at the distal housing end with a bore extending longitudinally through the nose, wherein the nose comprises an outer ramping surface extending distally and inwardly toward the bore from a proximal nose end adjacent to the housing to a distal nose end;
   c) an expandable dome comprising a dome length extending distally and inwardly from a proximal end adjacent to the housing to an apex of the dome, wherein the inner dome surface comprises a coping surface extending from the proximal end part way along the dome length to a distal bore leading to the apex, the dome being supported on the nose with the inner coping surface contacting the outer ramp surface of the nose;
   d) an O-ring, having a curved cross-section, supported in an annular groove provided in the outer dome surface adjacent to the proximal dome end;
   e) a drive train at least partially housed inside the housing, the drive train comprising:
      i) a first lever comprising a first lever proximal end spaced apart from a first lever distal end located adjacent to the distal housing end;
      ii) a second lever comprising a second lever proximal end located adjacent to the proximal housing end and spaced apart from a second lever distal end;
      iii) a drive rod comprising a drive rod proximal end space apart from a drive rod distal end, wherein the second lever distal end is in a universal joint relationship with the first lever proximal end, and wherein the first lever distal end is in a universal joint relationship with the drive rod proximal end and the drive rod distal end extends through the bore of the frusto-conical nose and connects to the expandable dome in the dome bore;
      iv) a first sleeve pivotably connected to the housing, wherein the first lever is in a slidable relationship with a first opening in the first sleeve disposed at an intermediate location between the first lever proximal end and the first lever distal end; and
      v) wherein the second lever is pivotably supported by the housing;
   f) a prosthesis cup contactable with the outer surface of the expandable dome;
   g) wherein the second lever proximal end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod to move along the longitudinal bore in the frusto-conical nose with the drive rod distal end moving from a first drive rod position spaced from the frusto-conical nose to a second drive rod position closer to the frusto-conical nose than the first drive rod position; and
   h) wherein this drive rod movement draws and expands the expandable dome supporting the O-ring against an interior surface of the prosthetic cup, thereby establishing a substantially friction tight engagement there between.

12. The inserter of claim 11 wherein the O-ring is positioned a distance x from the proximal end of the expandable dome, the distance x being from about 1 to about 25 percent of y, which is the distance along the longitudinal axis from the proximal end to the apex of the expandable dome.

13. The inserter of claim 11 wherein a knob is attached to the second lever proximal end, the knob enabling a user to manipulate the drive train.

14. The inserter of claim 11 wherein the material of the frusto-conical nose is selected from the group consisting of a polymer, a metal, and a ceramic.

15. The inserter of claim 11 wherein the expandable dome is made of a polymeric material.

16. A surgical kit for minimally invasive surgery, the kit including:
   a) a case having recesses into which components of the kit may be conveniently stored until use;
   b) at least one prosthetic cup implant; and
   c) an inserter for aiding a surgeon in controlling the installation of the orthopedic implant, the inserter comprising:
      i) a housing extending from a proximal housing end to a distal housing end;
      ii) a nose supported at the distal housing end with a bore extending longitudinally through the nose, wherein the nose comprises an outer ramping surface extending distally and inwardly toward the bore from a proximal nose adjacent to the housing to a distal nose end;
      iii) an expandable dome comprising a dome length extending distally and inwardly from a proximal end adjacent to the housing to an apex of the dome, wherein the inner dome surface comprises a coping surface extending from the proximal end part way along the dome length toward the apex, the dome being supported on the nose with the inner coping surface contacting the outer ramp surface of the nose;
      iv) an O-ring supported in an annular groove provided in the outer dome surface;
      v) a first lever comprising a first lever proximal end spaced apart from a first lever distal end located adjacent to the distal housing end;
      vi) a second lever comprising a second lever proximal end located adjacent to the proximal housing end and spaced apart from a second lever distal end;
      vii) a drive rod comprising a drive rod proximal end space apart from a drive rod distal end, wherein the second lever distal end is in a universal joint relationship with the first lever proximal end, and wherein the first lever distal, end is in a universal joint relationship with the drive rod proximal end and the drive rod distal end extends through the bore of the nose and connects to the dome in the dome bore;
      viii) a first sleeve pivotably connected to the housing, wherein the first lever is in a slidable relationship with a first opening in the first sleeve disposed at an intermediate location between the first lever proximal end and the first lever distal end;
      ix) wherein the second lever is pivotably supported by the housing; and
   d) wherein the second lever proximal end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod to move along the longitudinal bore of the nose with the drive rod distal end connected to the dome moving from a first drive rod position spaced from the inserter head to a second drive rod position closer to the nose than the first drive rod position; and e) wherein the prosthesis cup implant is removeably secured to the distal end of the expandable dome such that actuation of the drive train draws the drive rod along the bore in the nose to thereby expand the expandable dome supporting the O-ring against an interior surface of the prosthetic cup into a substantially friction tight engagement therebetween with the prosthesis cup being substantially incapable of movement with respect to the expandable dome and the O-ring.

17. The inserter of claim 16 wherein the O-ring is positioned around the outside circumference of the expandable dome a distance x from the proximal end of the expandable dome, the distance x being from about 1 to about 25 percent of y, which is the distance along a longitudinal axis from the proximal end to the apex of the expandable dome.

18. An inserter for aiding a surgeon in controlling the installation of an orthopedic prosthesis, the inserter comprising:
   a) a housing extending from a proximal housing end to a distal housing end;
   b) a frusto-conical nose supported at the distal housing end with a bore extending longitudinally through the nose, wherein the nose comprises an outer ramping surface extending distally and inwardly toward the bore from a proximal nose end adjacent to the housing to a distal nose end;
   c) an expandable dome comprising a dome length extending distally and inwardly from a proximal end adjacent to the housing to an apex of the dome, wherein the inner dome surface comprises a coping surface extending from the proximal end part way along the dome length toward the apex, the dome being supported on the nose with the inner coping surface contacting the outer ramp surface of the nose;
   d) an O-ring supported in an annular groove provided in the outer dome surface, the O-ring positioned a distance x from the proximal end of the expandable dome, the distance x being from about 1 to about 25 percent of y, which is the distance along the longitudinal axis from the proximal end to the apex of the expandable dome;
   e) a drive train at least partially housed inside the housing, the drive train comprising:
      i) a first lever comprising a first lever proximal end spaced apart from a first lever distal end located adjacent to the distal housing end;
      ii) a second lever comprising a second lever proximal end located adjacent to the proximal housing end and spaced apart from a second lever distal end;
      iii) a drive rod comprising a drive rod proximal end space apart from a drive rod distal end, wherein the second lever distal end is in a universal joint relationship with the first lever proximal end, and wherein the first lever distal end is in a universal joint relationship with the drive rod proximal end and the drive rod distal end extends through the bore of the frusto-conical nose and connects to the expandable dome in the dome bore;
      iv) a first sleeve pivotably connected to the housing, wherein the first lever is in a slidable relationship with a first opening in the first sleeve disposed at an intermediate location between the first lever proximal end and the first lever distal end,
      v) wherein the second lever is pivotably supported by the housing; and
   f) wherein the second lever proximal end is manipulable from a first position spaced from the housing to a second position spaced closer to the housing than the first spaced position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the drive rod to move along the longitudinal bore in the frusto-conical nose with the drive rod distal end connected to the dome moving from a first drive rod position spaced from the frusto-conical nose to a second drive rod position closer to the frusto-conical nose than the first drive rod position; and
   g) wherein this drive rod movement draws and expands the expandable dome outer surface supporting the O-ring.

19. The inserter of claim 18 wherein a portion of the O-ring extends above the outer dome surface.

20. The inserter of claim 18 wherein the O-ring and the dome are made of a polymeric material.

21. An inserter, comprising:
   a) a housing extending from a proximal housing end to a distal housing end;
   b) a nose supported at the distal housing end with a bore extending longitudinally through the nose, wherein the nose comprises an outer ramping surface extending distally and inwardly toward the bore from a proximal nose end adjacent to the housing to a distal nose end;
   c) an expandable dome comprising a dome length extending distally and inwardly from a proximal end adjacent to the housing to an apex of the dome, wherein the inner dome surface comprises a coping surface extending from the proximal end part way along the dome length toward the apex, the dome being supported on the nose with the inner coping surface contacting the outer ramp surface of the nose;
   d) an O-ring supported in an annular groove provided in the outer dome surface; and
   e) a drive train at least partially housed inside the housing, the drive train comprising a drive rod comprising a drive rod proximal end space apart from a drive rod distal end that is connected to the nose, wherein the drive rod distal end extends through the nose of the inserter along the longitudinal axis and into the expandable dome through a central bore which begins at the distal cavity dome end and extends proximally therefrom,
   f) wherein the drive train is manipulable to cause the drive rod to move along the longitudinal bore in the nose with the drive rod distal end moving from a first drive rod position spaced from the nose to a second drive rod position closer to the nose than the first drive rod position to thereby cause the inner coping surface of the dome to move proximally against, the outer ramp surface of the nose and cause the dome supporting the O-ring to both expand from a first, unexpanded state to a second expanded state.

22. The inserter of claim 21 wherein expansion of the dome supporting the O-ring is sufficient to establish a substantially friction tight engagement against the interior surface of a prosthesis.

* * * * *